US010149924B1

(12) United States Patent
Datt et al.

(10) Patent No.: US 10,149,924 B1
(45) Date of Patent: Dec. 11, 2018

(54) READY TO USE BIODEGRADABLE AND BIOCOMPATIBLE ARTIFICIAL SKIN SUBSTITUTE AND A METHOD OF PREPARATION THEREOF

(71) Applicants: DATT MEDIPRODUCTS LIMITED, New Delhi (IN); DATT LIFE SCIENCE PVT. LTD., New Delhi (IN)

(72) Inventors: Rajan Datt, New Delhi (IN); Siddharth Pandey, New Delhi (IN); Pallavi Shrivastava, New Delhi (IN); Supriya Srivastava, New Delhi (IN)

(73) Assignees: DATT MEDIPRODUCTS LIMITED, New Delhi (IN); DATT LIFE SCIENCE PVT. LTD., New Delhi (IN)

( * ) Notice: Subject to any disclaimer, the term of this patent is extended or adjusted under 35 U.S.C. 154(b) by 0 days.

(21) Appl. No.: 16/108,155

(22) Filed: Aug. 22, 2018

Related U.S. Application Data

(63) Continuation of application No. 16/009,468, filed on Jun. 15, 2018, now Pat. No. 10,098,986, which is a
(Continued)

(30) Foreign Application Priority Data

Nov. 28, 2016 (IN) .............................. 201611040491

(51) Int. Cl.
*A61K 9/00* (2006.01)
*A61L 27/60* (2006.01)
(Continued)

(52) U.S. Cl.
CPC ............... *A61L 27/60* (2013.01); *A61L 27/26* (2013.01); *A61L 27/3633* (2013.01);
(Continued)

(58) Field of Classification Search
CPC ..................................................... A61L 27/60
See application file for complete search history.

(56) References Cited

U.S. PATENT DOCUMENTS

| 4,485,096 A | 11/1984 | Bell |
| 4,963,489 A | 10/1990 | Naughton et al. |
| | (Continued) | |

FOREIGN PATENT DOCUMENTS

| CN | 101361989 | 2/2009 |
| CN | 101361990 | 2/2009 |
| | (Continued) | |

OTHER PUBLICATIONS

Tai et al., "The Use of a Polyelectrolyte Fibrous Scaffold to Deliver Differentiated hMSCs to the Liver," Biomaterials 31 (2010); pp. 48-57. * See Priority U.S. Appl. No. 16/009,468, filed Jun. 15, 2018 * .

(Continued)

*Primary Examiner* — Paul W Dickinson
(74) *Attorney, Agent, or Firm* — Allen, Dyer, Doppelt + Gilchrist, P.A.

(57) ABSTRACT

The present invention relates to a three-dimensional cell culture system which can be used to culture a variety of different cells (Human mesenchymal stem cells, Human fibroblast, Keratinocytes, fibroblast differentiated form mesenchymal stem cells in vitro and keratinocytes differentiated form mesenchymal stem cells in vitro) in vitro for continued periods of time. In the present invention, mesenchymal stem cells (MSCs) derived from bone marrow or umbilical cord are inoculated and grown on a pre-established scaffold or matrix made up of chitosan and gelatin. The developed tissue constructs contain cells, growth factors, cytokines and other regulatory factors secreted by cells. The developed bioengineered tissue constructs provide the support, growth factors and essential cytokines for wound healing. Devel-
(Continued)

oped tissue construct useful in the treatment of burns wound, diabetic foot ulcer wound and type of chronic skin wounds. It is helpful in healing and regeneration of skin tissue.

15 Claims, 4 Drawing Sheets

Related U.S. Application Data continuation of application No. 15/485,358, filed on Apr. 12, 2017, now Pat. No. 10,004,830.

(51) Int. Cl.
| | | |
|---|---|---|
| *A61L 27/36* | (2006.01) | |
| *A61L 27/26* | (2006.01) | |
| *A61L 27/48* | (2006.01) | |
| *A61L 27/54* | (2006.01) | |
| *A61L 27/56* | (2006.01) | |
| *A61L 27/38* | (2006.01) | |

(52) U.S. Cl.
CPC .......... *A61L 27/3834* (2013.01); *A61L 27/48* (2013.01); *A61L 27/54* (2013.01); *A61L 27/56* (2013.01); *A61L 2300/252* (2013.01); *A61L 2300/414* (2013.01)

(56) References Cited

U.S. PATENT DOCUMENTS

| | | | |
|---|---|---|---|
| 5,882,521 | A | 3/1999 | Bouvier et al. |
| 6,497,875 | B1 | 12/2002 | Sorrell et al. |
| 6,790,455 | B2 | 9/2004 | Chu et al. |
| 6,933,326 | B1 | 8/2005 | Griffey et al. |
| 8,287,854 | B2 | 10/2012 | Phan |
| 8,691,946 | B2 | 4/2014 | Sanford et al. |
| 8,779,089 | B2 | 7/2014 | Sanford et al. |
| 8,790,921 | B2 | 7/2014 | Lelkes et al. |
| 9,155,607 | B2 | 10/2015 | Nauman et al. |
| 9,217,129 | B2 | 12/2015 | Moretti et al. |
| 9,220,757 | B2 | 12/2015 | Lee et al. |
| 10,004,830 | B2 | 6/2018 | Datt et al. |
| 2012/0149111 | A1 | 6/2012 | Wegst et al. |
| 2013/0243882 | A1 | 9/2013 | Fu et al. |
| 2014/0341865 | A1 | 11/2014 | Jeon et al. |
| 2016/0129045 | A1 | 5/2016 | Jeon et al. |
| 2017/0320809 | A1 | 11/2017 | Hasegawa et al. |
| 2018/0147324 | A1 | 5/2018 | Datt et al. |

FOREIGN PATENT DOCUMENTS

| | | |
|---|---|---|
| CN | 102172337 | 9/2011 |
| CN | 104263699 | 1/2015 |
| CN | 104312970 | 1/2015 |
| KR | 10-2015-0088228 | 7/2015 |
| WO | 2016/072435 | 5/2016 |

OTHER PUBLICATIONS

Gohari et al., "Evaluation of Tissue-Engineered Skin (Human Skin Substitute) and Secondary Intention Healing in the Treatment of Full Thickness Wounds after Mohs Micrographic or Excisional Surgery," Dermatol Surg. 28 (12): 1107-1114; Dec. 2002; Abstract Only; 2 pages. * See Priority U.S. Appl. No. 16/009,468, filed Jun. 15, 2018 * .
Krishnamoorthy et al., "Specific Growth Factors and the Healing of Chronic Wounds," Journal of Wound Care, vol. 10, No. 5; May 2001; First Page Only. * See Priority U.S. Appl. No. 16/009,468, filed Jun. 15, 2018 * .
Martin et al., "Effect of Human Fibroblast-Derived Dermis on Expansion of Tissue From Venous Leg Ulcers," Wound Repair and Regeneration, 11:292-296; Published Jul. 9, 2003; Abstract Only; 2 pages. * See Priority U.S. Appl. No. 16/009,468, filed Jun. 15, 2018 * .
Shen et al., "Innovative Therapies in Wound Healing," Journal of Cutaneous Medicine and Surgery; vol. 7, Issue 3; pp. 217-224; Published May 1, 2003; Abstract Only; 2 pages. * See Priority U.S. Appl. No. 16/009,468, filed Jun. 15, 2018 *.
Werner et al., "Regulation of Wound Healing by Growth Factors and Cytokines," Physiol Rev. 83(3): 835-70; Jul. 2003; Abstract Only; 1 page. * See Priority U.S. Appl. No. 16/009,468, filed Jun. 15, 2018 *.
Mansbridge et al., "Three-Dimensional Fibroblast Culture Implant for the Treatment of Diabetic Foot Ulcers: Metabolic Activity and Therapeutic Range," Tissue Eng. 4(4): 403-414; Winter 1998; Abstract Only; 1 page. * See Priority U.S. Appl. No. 16/009,468, filed Jun. 15, 2018 *.
Osborne et al., "Epidermal-Dermal Interactions Regulate Gelatinase Activity in Apligraf, A Tissue-Engineered Human Skin Equivalent," Br J. Dermatol. 146(1): 26-31; Jan. 2002; Abstract Only; 2 pages. * See Priority U.S. Appl. No. 16/009,468, filed Jun. 15, 2018 *.
O'Connor et al., "Grafting of Burns With Cultured Epithelium Prepared From Autologous Epidermal Cells," The Lancet, vol. 317, Issue 8211; Jan. 10, 1981; pp. 75-78; Abstract Only; 2 pages. * See Priority U.S. Appl. No. 16/009,468, filed Jun. 15, 2018 *.
Madden et al., "Grafting of Cultured Allogeneic Epidermis on Second- and Third-Degree Burn Wounds on 26 Patients," J. Trauma. 26(11): 955-62; Nov. 1986; Abstract Only; 1 page. * See Priority U.S. Appl. No. 16/009,468, filed Jun. 15, 2018 *.
Rheinwald et al., "Serial Cultivation of Strains of Human Epidermal Keratinocytes: The Formation of Keratinizing Colonies from Single Cells," Cell. 6(3): 331-43; Nov. 1975; Abstract Only; 1 page. * See Priority U.S. Appl. No. 16/009,468, filed Jun. 15, 2018 *.
Compton et al., "Skin Regenerated From Cultured Epithelial Autografts on Full-Thickness Burn Wounds From 6 Days to 5 Years After Grafting. A Light, Electron Microscopic and Immunohistochemical Study," Lab Invest. 60(5): 600-12; May 1989; Abstract Only; 2 pages. * See Priority U.S. Appl. No. 16/009,468, filed Jun. 15, 2018 *.
Desai et al., "Lack of Long-Term Durability of Cultured Keratinocyte Burn-Wound Coverage: A Case Report," J Burn Care Rehabil. 12(6): 540-5; Nov.-Dec. 1991; Abstract Only; 1 page. * See Priority U.S. Appl. No. 16/009,468, filed Jun. 15, 2018 *.
Ronfard et al., "Use of Human Keratinocytes Cultured on Fibrin Glue in the Treatment of Burn Wounds," Burns. 17(3): 181-4; Jun. 1991; Abstract Only; 1 page. * See Priority U.S. Appl. No. 16/009,468, filed Jun. 15, 2018 *.
Wright et al., "Alternative Delivery of Keratinocytes Using a Polyurethane Membrane and the Implications for its Use in the Treatment of Full-Thickness Burn Injury," Burns. 24(1): 7-17; Feb. 1998; Abstract Only; 2 pages. * See Priority U.S. Appl. No. 16/009,468, filed Jun. 15, 2018 *.
Kaiser et al., "Cultured Autologous Keratinocytes in Fibrin Glue Suspension, Exclusively and Combined with STS-Allograft (Preliminary Clinical and Histological Report of a New Technique)," Burns, vol. 20, Issue 1, Feb. 1994, pp. 23-29; Abstract Only; 2 pages. * See Priority U.S. Appl. No. 16/009,468, filed Jun. 15, 2018 *.

READY TO USE BIODEGRADABLE AND BIOCOMPATIBLE ARTIFICIAL SKIN SUBSTITUTE AND A METHOD OF PREPARATION THEREOF

CROSS REFERENCE TO RELATED APPLICATION

This is a continuation application based on U.S. patent application Ser. No. 16/009,468 filed on Jun. 15, 2018, which is based on a continuation application of U.S. patent application Ser. No. 15/485,358 filed on Apr. 12, 2017 (now U.S. Pat. No. 10,004,830), which claims priority to Indian Patent Application No. 201611040491 filed on Nov. 28, 2016, the disclosures which are hereby incorporated by reference in their entirety.

BACKGROUND OF THE INVENTION

Field of the Invention

The present invention relates to the field of tissue engineering.

More particularly, the invention relates an in-vitro method for inducing cells to produce an extracellular matrix.

More particularly, the invention relates to a living extracellular matrix, which has tissue like properties and is capable of being used for wound healing.

More particularly, the invention relates to an extracellular matrix for the treatment of burn wound, diabetic foot ulcer and other chronic wounds.

Description of the Related Art

The field of tissue engineering combines bioengineering methods with the principles of life sciences to understand the structural and functional relationships in normal and pathological mammalian tissues. The goal of tissue engineering is the development and ultimate application of biological substitutes to restore, maintain, or improve tissue functions. Thus, through tissue engineering, it is possible to design and manufacture a bioengineered tissue construct in vitro. Bioengineered tissues construct include cells that are associated with a human tissues and natural matrix/scaffold. The new bioengineered tissue must be functional when grafted onto a host, and be permanently incorporated within the host's body or progressively bio-remodeled by cells from the recipient host patient. Fabrication of a tissue equivalent without a support member or scaffold leads to scientific challenges in creating the new bioengineered tissue.

The primary goal in the treatment of wounds is to achieve wound closure for which several modalities have been developed. One of the persistent problems in the treatment of large wounds, like burns, is the availability of skin cover to repair damaged areas.

The treatment adopted depends on the type of wound and the physician's approach. Postoperative wounds are typically categorized into primary intention (surgical closure), secondary intention (wound left open to close by reparative process) and tertiary closure (left open, usually because of infection, and closed surgically at a later date). In primary intention the physician approximates the wound edges resulting in minimal scar formation.

Secondary intention wound treatment usually occurs when there are, for example, (a) gaping wounds with lacerated edges, (b) large defects that cannot be covered by grafting, (c) extensive trophic disturbances such as leg ulcers, (d) highly suppurative wounds, (e) wounds interspersed with foreign bodies, (f) infected wounds that have undergone primary closure, and (g) wounds that heal better cosmetically and functionally as a result of contraction rather than sutures, e.g. fingertip injuries. With secondary intention wound treatment, the loss of tissue has to be compensated by the formation of new connective tissue and wound contraction. Scar formation under such conditions can often result in a cosmetically and functionally inferior scar. In these situations, sealing of epithelium across the wound does not occur rapidly as the cells have to grow down and spread progressively across the wound at the junction of viable and nonviable tissue. There is also more granulation tissue formation growing from the base of the wound to fill the defect. This is accompanied by wound contraction, causing the end result to be an intact epithelium (regeneration). However, more tissue distortion and an extensive, cosmetically unsatisfactory, scar often causes an impairment of function (repair) (Goepel J R. "Responses to cellular injury," In: Underwood J C E (ed). General and Systemic Pathology, Second Edition. London, UK, Churchill Livingstone, 1996, pp 121122.). Repair indicates the process that a tissue undergoes to completely regenerate/reform. Allogeneic keratinocytes used in this wound cover of the present invention are meant to repair the damaged skin leading to its regeneration.

In mammalian skin, this type of tissue injury initiates a complex but orderly series of biochemical and cellular events that are influenced by a large number of chemical mediators, leading to haemostasis, wound healing and the eventual generation of the scar tissue. The repair process can be arbitrarily divided into three main overlapping and inter-relating phases: inflammation; new tissue formation (proliferation); and matrix formation and remodeling. (Clark R A F. Wound repair; overview and general considerations. In: Clark R A F (ed). The Molecular and Cellular Biology of Wound Repair, Second Edition. London, UK, Plenum Press, 1996, pp 350)). It should be emphasized that there is no clear demarcation between the phases of wound healing, as the process of tissue repair is a continuous phenomenon.

Wound healing of the skin is thus a complex biological process that requires the restoration of cover by re-epithelialization and restoration of support by dermal fibroblasts. Re-epithelialization results from keratinocyte migration and proliferation. The rate of re-epithelialization is higher in superficial wounds as compared to deeper wounds wherein the chances of infection and scar formation are very high. While the primary end point of healing is the wound closure, the focus on the quality of healing is also important.

Tissue engineered skin substitutes are a significant advance in the field of wound healing. These were developed due to limitations associated with the use of autografts, including the creation of a donor site, which is at risk of developing pain, scarring, infection and/or slow healing, for example.

Prior to the development of tissue engineered skin, the only available options were split or full thickness skin grafts, tissue flaps or free tissue transfers. Over the last two decades' tissue engineered skin substitutes have been developed and their use has progressed at a very rapid rate. Tissue engineering was defined in 1987 by the National Science Foundation bioengineering panel meeting in Washington, D.C., USA, as "the application of the principles and methods of engineering and the life sciences toward the development of biological substitutes to restore, maintain, or improve function." Today, tissue engineered skin products have been approved for use by the US Food and Drug Administration (FDA) and others are undergoing testing and regulatory review. Tissue engineered skin substitutes offer the promise of tissue replacement without requiring a donor site and may produce better healing. Tissue engineered skin may function by providing at the wound site the needed matrix materials or cells required for the healing process. Tissue engineered skin refers to skin products made mainly of cells, or extra-cellular matrix materials only, or to a combination of cells and matrices.

Cell sources for tissue engineering fall into three categories: autologous cells (from the patient); allogeneic cells (from a human donor, but not immunologically identical); and xenogeneic cells (donor from a different species). Each of these origins may further be delineated into adult or embryonic stem cells, or "differentiated" cells obtained from tissue, where the cell population comprises of mixture of differently matured cells that includes rare stem and progenitor cells. To date, the available therapies depend on the whole cell mix, or separation of enrichment of stem cells. While autologous tissue transfers can be highly effective in securing wound healing, such procedures (e.g., grafts and flaps) are invasive, painful, and expensive, and are not within the purview of many wound care practitioners. Autologous skin grafts, though successful, have limitations due to the limited donor sites as well as creation of fresh wounds at the donor site. To overcome this, several types of skin substitutes such as allogenic or xenogenic skin grafts have been used with varying degrees of success. Limitations of this treatment are related to sterility, difficulty in handling, risk of viral transmission and immune rejection by the host.

Cell based wound therapies, such as cellular skin substitutes, have the potential to reduce wound contraction and to influence the nature of the final healed tissue. Reports are available that indicate additional benefits of skin substitute therapy besides early wound closure. The property of the healed wound that closely resembles those of normal uninjured skin (Gohari et al., "Evaluation of tissue engineered skin (human skin substitute) and secondary intention healing in the treatment of full thickness wounds after Mohs micrographic or excisional surgery," Dermatol Surg 28:110714, 2002.) It is believed that cells applied to the wound surface are "smart" and will bathe the wound bed with balanced cocktails of such mediators appropriate for the particular physiology of the wound environment that is sensed. Cells are thus advantageous over therapy provided by exogenous application of growth factors. (Krishnamoorthy et al. "Specific growth factors and the healing of chronic wounds," J Wound Care 10:1738, 2001). For example, incubation of cells derived from biopsies of venous ulcers in conditioned medium supernatant from human fibroblast cell culture induces a highly significant increase in skin cell proliferation, and this effect has been correlated with levels of several cytokines (Martin et al. "Effect of human fibroblast derived dermis on expansion of tissue from venous leg ulcers," Wound Repair Regen 11:2926, 2003.)

A bioengineered skin substitute has been to shown to act as an interactive "drug" delivery system (Shen et al. "Innovative therapies in wound healing," J Cutan Med Surg 2003 7(1) 217224) Werner et al. and Mansbridge et al. have reported that the viability and metabolic activity of the cellular component of a cellular skin substitute is essential for therapeutic efficacy. These groups have proposed that this is due to the need for ongoing cytokine expression in the wound bed following application. (Werner et al. "Regulation of wound healing by growth factors and cytokines," Physiol Rev 83:83570, 2003 Mansbridge et al. "Three-dimensional fibroblast culture implant for the treatment of diabetic foot ulcers: metabolic activity and therapeutic range," Tissue Engineering 4:40314, 1998). Measurements of matrix metallo-proteinases (MMPs) secreted by the epidermis and dermis of LSE (Living skin equivalent) show that the individual layers of bioengineered skin sense their environment and secrete MMP's in different quantities and ratios depending upon their environment. (Osborne et al. "Epidermal-dermal interactions regulate gelatinase activity in Apligraf, a tissue engineered human skin equivalent," Br J Dermatol 146:2631, 2002.) Apligraf™ (U.S. Pat. No. 4,485,096) is made from human fibroblasts grown on a semipermeable membrane with bovine type I collagen, then overlayed with keratinocytes, which are grown until a confluent layer forms. The keratinocytes and dermal fibroblasts are derived from neonatal foreskin and propagated in culture. Subsequently, keratinocytes overlying the epidermis are exposed to an air liquid interface to promote formation of a stratum corneum. The process takes 20 days to be ready for application to the wound. Epidermal substitutes prepared from keratinocytes obtained from the skin sample of the future recipient (autografts) are shown to have the ability to reconstitute an epidermis when delivered to an area of skin loss such as the excised bed of a burn eschar. (O'Conner et al. "Grafting of burns with cultured epithelium prepared from autologous epidermal cells," Lancet 1:7578, 1981) or from another person (allografts) (Madden et al. "Grafting of cultured allogeneic epidermis on second and third degree burn wounds on patients," J Trauma 26(11):95562, 1986.) Following the pioneering work of Rheinwald and Green. ("Serial cultivation of strains of human epidermal keratinocytes: the formation of keratinizing colonies from cells," Cell 6:331344, 1975), it is now possible to serially propagate normal human keratinocytes in vitro. These keratinocytes can reconstitute a stratified squamous epithelium, which maintains the biochemical, morphological and functional characteristics of a native epidermis (Compton et al. "Skin regenerated from cultured epithelial autografts on full thickness burn wounds from 6 days to 5 years after grafting. A light, electron microscopic and immunohistochemical study," Lab. Invest 60:600612, 1989). Established methods for in vitro culturing of epithelial grafts necessitate the growth of multilayered cells. This procedure requires a period of 34 weeks before the films are ready for transplantation. The grafting of such labor intensive sheets has however faced mixed fortunes, with reports of lower than anticipated efficiencies (Desai et al. "Lack of longterm durability of cultured keratinocyte burn wound coverage: a case report," J Burn Care Rehabil. 12(6):5405, 1991). Problems with the lack of "take" and long term durability, time required for film preparation and high cost to produce such grafts, as well as difficulty in handling have led to the development of alternate delivery systems to transfer eratinocytes to the wound bed.

Cultured Epidermal Autografts (Epicel™) have been described as an in-vitro cultured epidermal keratinocytes using a feeder layer of irradiated murine fibroblasts. A minimum of 2 to 3 weeks is required, from the time of biopsy collection to delivery of grafts Though these cultured epidermal autografts provides permanent wound coverage, a decreased requirement for donor sites, rapid coverage of the wound, faster pain relief, and a better functional and cosmetic outcome. However, the limitations of this graft include a 3-week delay for graft cultivation, the lack of a dermal component, and high cost.

Cultured epidermal allografts can be made in a similar process as Epicel™, derived from unrelated allogeneic donors, such as newborn foreskin. Since the cells can be grown in advance and stockpiled, the cells are readily available for grafting. They are not commercially viable. Such similar products contain non-proliferating, differentiated cells. As a result, they provide a cover only up to its limited area. However, there is a need to require proliferative cells that on migrating into the wound bed would be able to proliferate and cover larger areas than that provided by the wound cover. The advantage of using cultured epidermal allografts is immediate graft availability. The disadvantages are that they do not survive permanently on the wound bed, and there is a possibility of disease transmission, which can be minimized with extensive screening.

An in vitro dermal replacement, Integra® is an artificial skin which consists of an artificial dermis (matrix of bovine collagen and chondroitin sulfate, a shark derived glycosaminoglycan) and a disposable silicone sheet (artificial epidermis). It is approved for its use in burns. The advantage of using this artificial dermis is that it allows a neodermis to develop. However, the disposable silicone sheet can allow the accumulation of exudate, increasing the risk of infection. It also does not provide a real epidermal component; and the silicone sheet must be surgically removed and ultimately replaced with an autograft or allograft.

Derma Graft™, is a tissue engineered skin substitute which comprises of collagen and glycosaminoglycans as a substrate for autologous cultured keratinocytes as the epidermal component, and collagen and glycosaminoglycan substrate inoculated with autologous fibroblasts as the dermal component. However, the overall 'take' was approximately 50% (attributed in part to proteases in the wound environment) which is not successful enough to make this a routinely acceptable skin replacement. The additional disadvantage of this skin substitute is the need to wait 3 to 4 weeks to produce the cultured grafts.

Another skin substitute, previously available as Transcyte™, comprises neonatal (allogeneic) fibroblasts which have been cultured and proliferate on nylon fibers embedded into a silastic coated with porcine collagen. After 4 to 6 weeks this forms a dense cellular 'tissue', which contains high levels of secreted human matrix proteins as well as multiple growth factors. The fibroblasts are rendered non-viable by freezing after synthesizing collagen extracellular matrix and growth factors. U.S. Pat. No. 6,790,455 describes a biodegradable and/or bioabsorbable matrix formed by electrospinning fibers of biodegradable and/or bioabsorbable fiberizable material physically associated with viable cells to contain and release the cells at a controlled rate. This technology has not been demonstrated to be effective at delivering keratinocytes or otherwise serving as a skin substitute. U.S. Pat. No. 6,933,326 describes the Nonliving Allogeneic Acellular Dermal Matrix (marketed as Alloderm®), which is manufactured by cutting sheets of dry tissue matrix into strips; cryofracturing the dry tissue matrix strips at cryogenic temperatures; and freeze drying the strips to remove any moisture that may have been absorbed to give a dry acellular tissue matrix.

In severely burnt patients, early wound excision and skin grafting plays a crucial role and has resulted in shortened hospitalization time, decreased complications, and increased survival. Conventional treatment of deep or full thickness burn wounds is achieved by using split thickness skin grafts (STSG) as wound coverage. However, disadvantages associated with this method include that it causes morbidity at the donor site and that there are limited donor sites in extensive burns. Several methods have been used for delivering highly proliferative keratinocytes. One way in which cells can be made available at the wound site is through the culture of keratinocytes on the surface of biodegradable membranes which, when placed on the wound would release the cells on breakdown. (Ronfard et al, "Use of human keratinocytes cultured on fibrin glue in the treatment of burn wounds," Burns 17(3): 1814, 1991). The second method involves the "upside-down" transfer of cells cultured on nonbiodegradable membranes. (Wright K A et al. "Alternative delivery of keratinocytes using a polyurethane membrane and the implications for its use in the treatment of full thickness burn injury," Burns 24(1):717, 1998). Studies performed on animals demonstrate the ability of keratinocytes to migrate from the membrane onto the wound bed and reconstitute an intact epidermis. Alternatively, a suspension of keratinocytes could be administered at the wound site after incorporating into fibrin glue (Kaiser et al. "Cultured Autologous keratinocytes in fibrin glue suspension, exclusively and combined with STS allograft (preliminary clinical and histological report of a new technique)," Burns 20(1): 239, 1994.)

Therefore, it is very important to provide solutions which can solve the above problems in innovative manner. The present invention aims to provide solution for the above-mentioned problems and provides a technique of culturing human epidermal cells into a proliferating, sub-confluent layer on a biocompatible membrane, to form sheets suitable for grafting.

Reference may be made to U.S. Pat. No. 4,963,489 titled "Three-dimensional cell and tissue culture system" dated 16 Oct. 1990. The present invention relates to a three-dimensional cell culture system which can be used to culture a variety of different cells and tissues in vitro for prolonged periods of time. In accordance with the invention, cells derived from a desired tissue are inoculated and grown on a pre-established stromal support matrix. The stromal support matrix comprises stromal cells, such as fibroblasts, grown to sub-confluence on a three-dimensional matrix. Stromal cells may also include other cells found in loose connective tissue such as endothelial cells, macrophages/monocytes, adipocytes, pericytes, reticular cells found in bone marrow stroma, etc. The stromal matrix provides the support, growth factors, and regulatory factors necessary to sustain long-term active proliferation of cells in culture. When grown in this three-dimensional system, the proliferating cells mature and segregate properly to form components of adult tissues analogous to counterparts found in vivo.

Reference may be made to U.S. Pat. No. 5,882,521 titled "Water-wettable chromatographic media for solid phase extraction" dated 16 Mar. 1999. A method for removing an organic solute from a solution, comprising contacting the solution with a polymer formed by copolymerizing one or more hydrophobic monomers and one or more hydrophilic monomers, whereby the solute is adsorbed onto the polymer. The solution can comprise a polar solvent such as a polar organic solvent or water or an aqueous buffer. The hydrophobic monomer can be, for example, divinylbenzene. The hydrophilic monomer can be, for example, a heterocyclic monomer, such as a vinyl-pyridine or N-vinylpyrrolidone.

Reference may be made to U.S. Pat. No. 8,790,921 titled "Alimentary protein-based scaffolds (APS) for wound healing, regenerative medicine and drug discovery" dated 29 Jul. 2014. The invention provides engineered biomaterials derived from plant products. The engineered biomaterials are useful for biomedical applications. The engineered biomaterials are able to support the growth of animal cells.

Reference may be made to U.S. Pat. No. 8,779,089 titled "Methods and compositions for soft tissue repair" dated 15

Jul. 2014. Compositions and methods for tissue repair are provided including cell binding peptides and growth factor binding peptides. The cell binding peptides bind to one or more of stem cells, fibroblasts, or endothelial cells. The growth factor binding peptides include platelet derived growth factor (PDGF) binding peptides and growth differentiation factor (GDF) binding peptides. The tissue for repair includes tendon, muscle, connective tissue, ligament, cardiac tissue, vascular tissue, or dermis. Implantable devices for tissue repair are provided to which the cell and growth factor binding peptides are attached, such as acellular extracellular matrix having attached binding peptide.

Reference may be made to U.S. Pat. No. 8,691,946 titled "Methods and compositions for soft tissue repair" dated 8 Apr. 2014. Compositions and methods for tissue repair are provided including cell binding peptides and growth factor binding peptides. The cell binding peptides bind to one or more of stem cells, fibroblasts, or endothelial cells. The growth factor binding peptides include platelet derived growth factor (PDGF) binding peptides and growth differentiation factor (GDF) binding peptides. The tissue for repair includes tendon, muscle, connective tissue, ligament, cardiac tissue, vascular tissue, or dermis. Implantable devices for tissue repair are provided to which the cell and growth factor binding peptides are attached, such as acellular extracellular matrix having attached binding peptide.

Reference may be made to U.S. Pat. No. 9,220,757 titled "Method for inducing in vivo migration of stem cell" dated 29 Dec. 2015. The present invention relates to an implantable composition for treating a damaged tissue and a method for inducing an in vivo migration of a cell for treatment to a damaged tissue region. The present invention treats the damaged tissue by inducing/promoting homing of a cell for tissue generation by implanting a biodegradable scaffold reacted with chemotactic factors (for example, IL-8 or MIP-3 alpha) to a damaged location (for example, joint cartilage or skin). Thus, the composition of the present invention can not only be applied to the treatment of a damaged bone tissue, a joint cartilage, or a skin tissue more conveniently and efficiently compared to the conventional technology, but can also be used as a useful treatment supplement agent in cell treatment using allogeneic cell by enabling efficient utilization of cell resources for treatment, the cell resources which are high in scarcity.

Reference may be made to U.S. Pat. No. 9,217,129 titled "Oscillating cell culture bioreactor" dated 22 Dec. 2015. Methods and devices for cell or tissue culture are provided. One aspect provides a bioreactor having a gas permeable, closed-loop chamber for cell or tissue culture, and an oscillating means for moving the gas permeable, closed-loop chamber bi-directionally along an axis horizontal to an axis normal to the closed-loop chamber to force convection of cells and fluid in the gas permeable, closed-loop chamber. The bioreactor optionally includes a tissue engineering scaffold, an inlet means, an outlet means, and integrated sensors. Another aspect provides a bioreactor having a plurality of gas permeable, closed-loop chambers for cell or tissue culture. Methods of culturing cells and producing tissue constructs are also provided.

Reference may be made to U.S. Pat. No. 9,155,607 titled "Compositions and methods for repair or regeneration of soft tissue" dated 30 Oct. 2015. Disclosed are bio-scaffolds and methods for use in soft tissue repair. The invention provides a biocompatible scaffold substantially free of mineralized bone comprising demineralized cancellous bone substantially devoid of all osteo-inductive factors, the demineralized cancellous bone comprising at least a first region and a second region, wherein a concentration gradient of crosslinks is configured to extend between the first region to the second region such that the concentration of the crosslinks in the first region is substantially higher than the concentration of the crosslinks in the second. The first region has increased mechanical strength relative to the second region. The first region comprising stiffened demineralized bone has greater resistance to enzymatic degradation relative to the second region.

Reference may be made to U.S. Pat. No. 8,287,854 titled "Skin equivalents derived from umbilical cord mesenchymal stem/progenitor cells and umbilical cord epithelial stem/progenitor cells" dated 16 Oct. 2012. The present invention relates to a skin equivalent and a method for producing the same, wherein the skin equivalent comprises a scaffold and stem/progenitor cells isolated from the amniotic membrane of umbilical cord. These stem/progenitor cells may be mesenchymal (UCMC) and/or epithelial (UCEC) stem cells, which may then be further differentiated to fibroblast and keratinocytes. Further described is a method for isolating stem/progenitor cells from the amniotic membrane of umbilical cord, wherein the method comprises separating the amniotic membrane from the other components of the umbilical cord in vitro, culturing the amniotic membrane tissue under conditions allowing cell proliferation, and isolating the stem/progenitor cells from the tissue cultures. The invention also refers to therapeutic uses of these skin equivalents. Another aspect of the invention relates to the generation of a mucin-producing cell using stem/progenitor cells obtained from the amniotic membrane of umbilical cord and therapeutic uses of such mucin-producing cells. In yet another aspect, the invention relates to a method for generating an insulin-producing cell using stem/progenitor cells isolated from the amniotic membrane of umbilical cord and therapeutic uses thereof. The invention further refers to a method of treating a bone or cartilage disorder using UCMC. Furthermore, the invention refers to a method of generating a dopamin and tyrosin hydroxylase as well as a HLA-G and hepatocytes using UCMC and/or UCEC. The present invention also refers to a method of inducing proliferation of aged keratinocytes using UCMC.

Reference may be made to U.S. Pat. No. 6,497,875 titled "Multilayer skin or dermal equivalent having a layer containing mesenchymal stem cells" dated 24 Dec. 2002. In this invention, a multilayer skin equivalent is formed having a scaffold layer containing dermis-forming cells, and a keratinocyte layer. The dermis-forming cells and keratinocytes are preferably autologous, and the dermis-forming cells can be human mesenchymal stem cells (MSCs), dermal fibroblasts (e.g., papillary or reticular dermal fibroblasts) or mixtures thereof. The scaffold is preferably type I collagen alone, or types I and II collagen in combination. Also formed is a multilayer skin equivalent having a scaffold layer containing a layer of extracellular matrix component containing papillary dermal fibroblasts in laminar relationship with a layer of extracellular matrix component containing reticular dermal fibroblasts, and a keratinocyte layer. A multilayer dermal equivalent is provided having a layer of extracellular matrix component containing papillary dermis-forming cells and a layer of extracellular matrix component containing reticular dermis-forming cells. In another embodiment, the dermal equivalent has a layer containing MSCs and a layer selected from a layer of extracellular matrix component containing papillary dermis-forming cells and a layer of extracellular matrix component containing reticular dermis-forming cells, and optionally a keratinocyte layer. In the skin and dermal equivalents, at least one layer may contain an agent that promotes adhesion or angiogenesis. There may also be a bioactive agent that enhances proliferation, commitment or differentiation of mesenchymal stem cells into dermal components, either in vitro or in vivo. An injectionable composition is also provided containing dermis-forming cells and an extracellular matrix component in a pharmaceutically acceptable injectable carrier.

Reference may be made to Application No. US2016129045 (A1) titled "COMPOSITION FOR WOUND-HEALING COMPRISING ADULT STEM CELLS AND ELASTIN-LIKE POLYPEPTIDES". Provided is a composition for wound-healing containing adult stem cells and elastin-like polypeptides, and more specifically, to a composition for wound-healing capable of effectively treating skin wounds by simultaneously administering elastin-like polypeptides along with adult stem cells thereby increasing the viability of the adult stem cells transplanted on the wounds and promoting angiogenesis.

Reference may be made to Application No. WO2016072435 (A1) titled "AGENT FOR MAINTAINING STEM CELLS IN UNDIFFERENTIATED STATE AND AGENT FOR PROMOTING GROWTH THEREOF". The present invention addresses the problem of finding a new substance capable of maintaining stem cells in an undifferentiated state while efficiently promoting the growth thereof, and providing said substance as an agent for maintaining stem cells in an undifferentiated state or as an agent for promoting the growth thereof. The present invention also addresses the problem of providing an inexpensive and highly safe wound healing agent that has a skin wound healing effect, and can be easily utilized in the fields of skin regeneration medicine and beauty care. The present invention is an agent for maintaining stem cells in an undifferentiated state, an agent for promoting the growth thereof, or a wound healing agent, and contains, as an active ingredient, a mixture of one or more fatty acid glycerides represented by general formula (I) (in the formula, at least one of R1, R2, and R3 is an acyl group derived from a C16-22 unsaturated fatty acid, and the remainder are a hydrogen atom or an acyl group derived from a saturated fatty acid).

Reference may be made to Application No. KR20150088228 (A) titled "COMPOSITIONS COMPRISING AMNIOTIC MESENCHYMAL STEM CELL FOR THE TREATMENT OF SKIN WOUND". The present invention relates to a pharmaceutical composition comprising amniotic mesenchymal stem cells, a pharmaceutically effective amount of the conditioned media and a pharmaceutically acceptable carrier for healing a skin wound. The amniotic mesenchymal stem cells according to the present invention, compared to hepatic mesenchymal stem cells, highly express and secret genes and proteins for angiogenesis, significantly increase the transfer of cells and promote the healing of the wound. In addition, the transplanted amniotic mesenchymal stem cells are highly engrafted to the skin wound and highly express keratinocyte-specific proteins, thereby being able to be advantageously used in healing a skin wound.

Reference may be made to Application No. CN104312970 (A) titled "Preparation method of clinical treatment level epidermal stem cell for cell therapy by applying human extracellular matrix screening and mass culture". The invention discloses culture, screening and amplification technology for clinical treatment level epidermal stem cells, and the bottlenecks have always been the hotspot and difficulty of research in the stem cell biology field; and currently, significant adhesion property of basement membrane is utilized for separation and purification, and three-dimensional culture amplification method is employed to obtain the cells. The invention is suitable for dependent amplification adherent type cells and provides three-dimensional high simulation of in vivo extracellular matrix system for screening and separation on target cell level. A novel biological cell culture technique comprising high simulation of in vivo adherent environment and in vitro culture of adult (embryo) skin stem cells. The high simulation of adherent environment of the extracellular matrix for screening and culturing object epidermal stem cells has the advantages of high passage capacity, high proliferation ability and formation of differentiation cortical structures in in vitro environment. The screened immunogenic cells securely acquire immune escape, have prolonged time of transplantation and increase tissue engineering clinical application. Therefore, the method provides absolutely advantaged solution for clinical treatment level cells for promoting wound healing and skin diseases.

Reference may be made to Application No. CN104263699 (A) titled "Culture method for large-scale preparation of clinical treatment level dermal multipotent stem cells for cell transplantation". The invention discloses a culture, screening and amplification technology of clinical treatment level dermal multipotent stem cells. These bottlenecks are always hot and difficult problems of research in the field of biological stem cells; at present, separation and purification are carried out by using the remarkable adhesion characteristic of a basement membrane, and the clinical treatment level dermal multipotent stem cells are obtained by adopting a three-dimensional culture and amplification means. The technology is applicable to the screening and separation of a target cell level by depending on amplifying adherent type cells and providing a three-dimensional high-simulation in-vivo extracellular matrix system. The technology is a novel biological cell culture technology, and adult (embryo skin) stem cells are subjected to in-vitro culture in a high-simulation in-vivo attached environment. The environment where a high-simulation substrate is located adheres, screens and cultures target dermal multipotent stem cells, so that the passage capability is high, the multiplication capacity is high, and a differentiated full-thickness dermal structure can be formed in an in-vitro environment. Immunogenic cells are screened out, so that immunologic escape is safely obtained, the transplantation time is prolonged, the clinical application of tissue engineering is improved, the healing of a surface of wound is promoted, and a clinical treatment level cellular solving scheme with absolute advantages is provided for skin diseases.

Reference may be made to Application No. US2014341865 (A1) titled "Dressing Material with Cell Components for Wound Healing". There is provided a dressing for treating a wound. The dressing for healing a wound can be useful in maintaining a moisture environment at a wound site using a biocompatible polymer scaffold, and effectively promoting healing of a wound by various growth factors secreted by skin cells or stem cells attached to the biocompatible polymer scaffold as well.

Reference may be made to Application No. US2013243882 (A1) titled "PHARMACEUTICAL COMPOSITION FOR TREATING SKIN WOUND". The present invention provides a method for treating a skin wound in a subject, which comprises administering the skin wound with a composition comprising umbilical mesenchymal stem cells. More particularly, the composition is used for improving wound healing.

Reference may be made to Application No. CN102172337 (A) titled "Tissue engineering skin with sebaceous gland-like structure and preparation method thereof". The invention provides tissue engineering skin with a sebaceous gland-like structure. In the tissue engineering skin, a dermis layer is formed by distributing placenta mesenchymal stem cells (PMSCs) in a gel solution, wherein the gel solution consists of an antigen-free extracellular matrix (ECM) and protein with for a function of forming a sebaceous gland structure through induction so that the gel solution has for a function of generating the sebaceous gland structure through induction; an epidermal layer consists of keratinized-induced amniotic epithelial cells (AECs) and non-induced AECs; and the sebaceous gland-like structure between the epidermal layer and the dermis layer is constructed by an AEC mass induced along the sebaceous gland direction. The tissue engineering skin is provided with the sebaceous gland-like structure and has application prospects of resisting bacteria, moistening skin and lowering post-transplantation infection risk. Animal experiments prove that the tissue engineering skin provided by the invention has the advantages of obviously improving healing rate and success rate for a transplantation wound surface, realizing wide cell source, strong multiplication capacity and more passage times, being beneficial to large-scale production of seed cells, and lowering the industrial cost.

Reference may be made to Application No. CN101361990 (A) titled "Double layer artificial skin and preparation method thereof". The invention discloses a double-layer artificial skin and a preparation method thereof, wherein, cell-free membranous biological derivative material is used as a surface layer, and a fibroblast, extracellular matrix synthesized and secreted by the fibroblast and a cell growth factor are compounded in the interior of biological support material to form a dermis, and then the surface layer and the dermis are combined to form the double-layer artificial skin; a compact surface layer structure can effectively reduce the loss of water, electrolytes and protein from surface of wound, avoid the invading and the reproduction of bacteria to the impaired surface of wound as well as the infection of the surface of wound, and be beneficial to epitheliosis and epithelial growth; the dermis can directly repair the surface of wound, promote the ingrowth of cells around the surface of wound and the angiogenesis, induce the differentiation from stem cells to skin cells and quicken wound healing; the artificial skin has the advantages of being capable of promoting the regeneration of skin, improving the elasticity, the flexibility and the mechanical abrasion resistance of skin after the surface of wound is healed, reducing excess scar tissues, controlling the contracture, having excellent biocompatibility, increasing the success rate of transplant and improving the quality of healing; the double-layer artificial skin has wide material resources and simple production method, and is applicable to the clinical treatment of skin defect caused by inflammation, ulcer, thermal burns, iatrogenicity and the like.

Reference may be made to Application No. CN101361989 (A) titled "Double membrane tissue patching material and preparation method thereof". The invention discloses a double-layer membranous tissue repair material and a preparation method thereof, wherein, a cell-free membranous biological derivative material is used as a surface layer, and a fibroblast is compounded in the interior of a biological support material to form a substrate, and then the surface layer and the substrate are combined in a chimeric way to form the double-layer membranous tissue repair material; a compact surface layer structure can effectively reduce the loss of water, electrolytes and protein from surface of wound, avoid the invading and the reproduction of bacteria to the impaired surface of wound as well as prevent the infection of the surface of wound, thus being beneficial to epitheliosis and epithelial growth; the substrate can directly repair the surface of wound, promote the ingrowth of cells around the surface of wound and the angiogenesis, induce the differentiation from stem cells to skin cells and quicken wound healing; compared with the existing products, the tissue repair material has the advantages of being capable of promoting the regeneration of skin, improving the elasticity, the flexibility and the mechanical abrasion resistance of skin after the surface of wound is healed, reducing hyperplasia of scar tissues, controlling the contracture, having excellent biocompatibility, increasing the success rate of transplant and improving the quality of healing; the invention has wide material resources and simple production method; the double-layer membranous tissue repair material prepared is applicable to the clinical treatment of skin defect caused by inflammation, ulcer, thermal burns, iatrogenicity and the like.

However, none of the inventions in prior art comprise novel and unique technique of culturing human Mesenchymal stem cells into a proliferating, sub-confluent layer on a biocompatible membrane to form sheets suitable for grafting as comprised in the present invention, the present invention provides a better, efficient, easy to use, cost effective ready to use biodegradable and biocompatible artificial skin substitute.

The present invention provides a novel and unique novel and unique technique of culturing human epidermal cells into a proliferating, sub-confluent layer on a biocompatible membrane to form sheets suitable for grafting. The invention provides a ready to use biodegradable and biocompatible tissue construct with autologous/allogeneic human stem cells based product. The present invention also provides a reconstructive procedure to meet the specific requirements necessary to achieve satisfactory wound closure and also to restore functional integrity in the least time and with the least complications and morbidity. The extracellular matrix as provided by the present invention has tissue like properties and is capable of being used for wound healing.

SUMMARY OF THE INVENTION

The primary objective of the invention is to provide artificial bioengineered tissue construct for rapid wound healing and tissue regeneration.

Another objective of the invention is to provide a ready to use biodegradable and biocompatible tissue construct with autologous/allogeneic human stem cells based product.

Another objective of the invention is to provide a method of preparation of such device.

A further objective of the invention is to develop artificial bioengineered tissue construct for burn wound healing and chronic wounds healing.

The present invention provides a novel and unique technique of culturing human Mesenchymal stem cells into a proliferating, sub-confluent layer on a biocompatible membrane to form sheets suitable for grafting. The invention provides a ready to use biodegradable and biocompatible tissue construct with autologous/allogeneic human stem cells based product. The present invention also provides a reconstructive procedure to meet the specific requirements necessary to achieve satisfactory wound closure and also to restore functional integrity in the least time and with the least complications and morbidity. The extracellular matrix as provided by the present invention has tissue like properties and is capable of being used for wound healing and tissue regeneration.

DETAILED DESCRIPTION OF THE SEVERAL EMBODIMENTS

Figure 1:
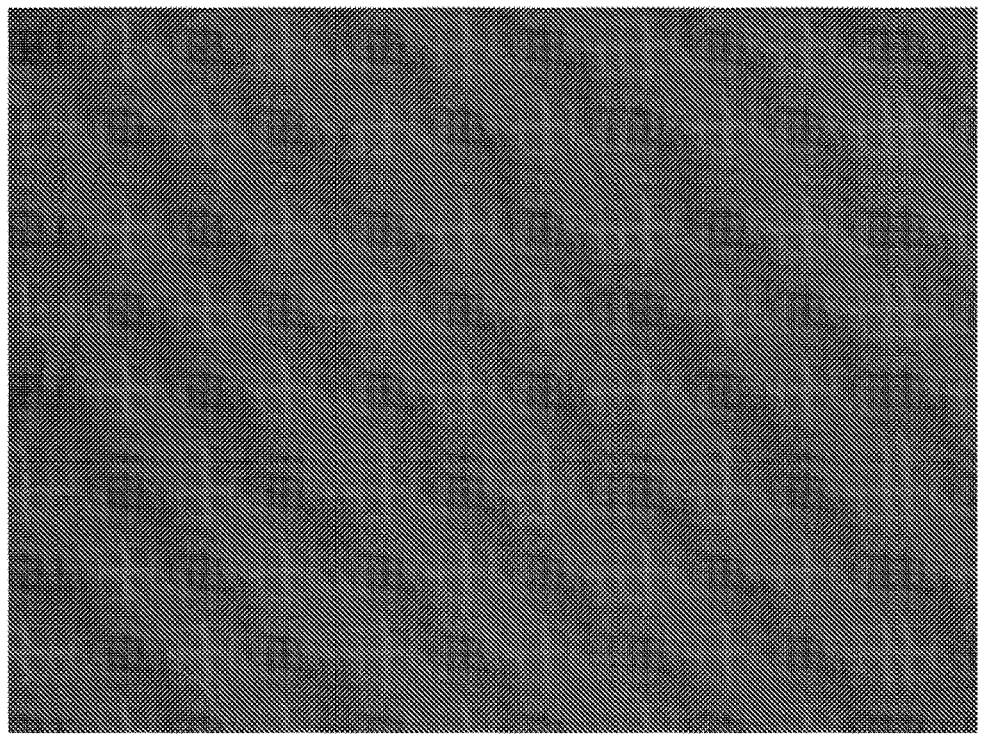
FIG. 1 shows the human mesenchymal stem cells cultured on developed matrix at Day 4.
Figure 2:
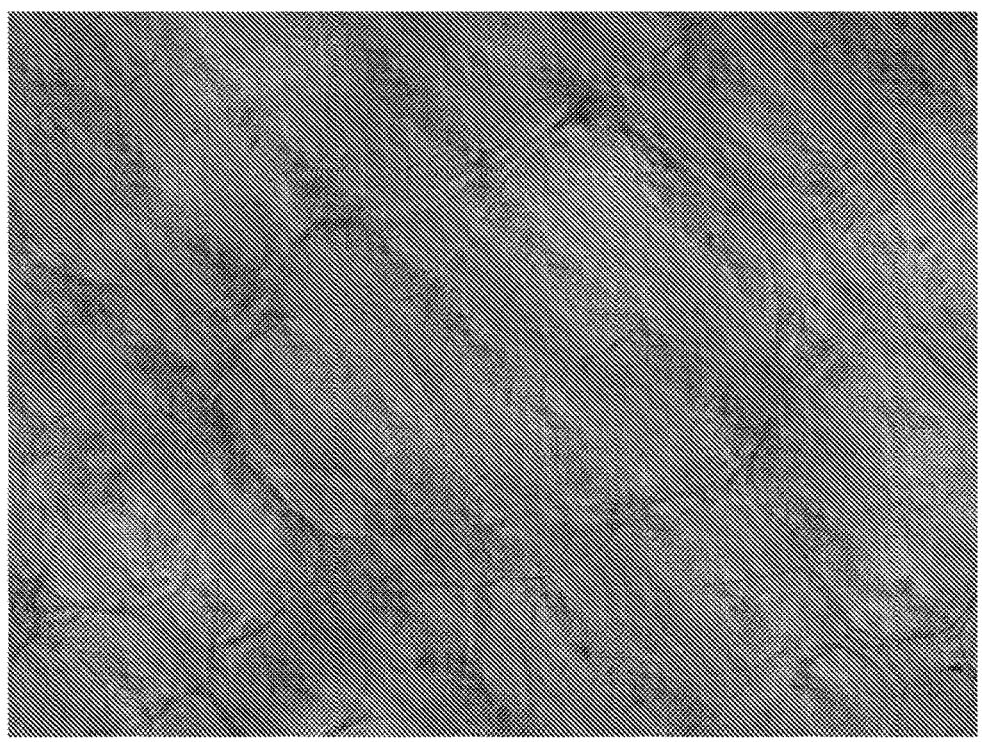
FIG. 2 shows the human mesenchymal stem cells cultured on developed matrix at Day 10.
Figure 3:
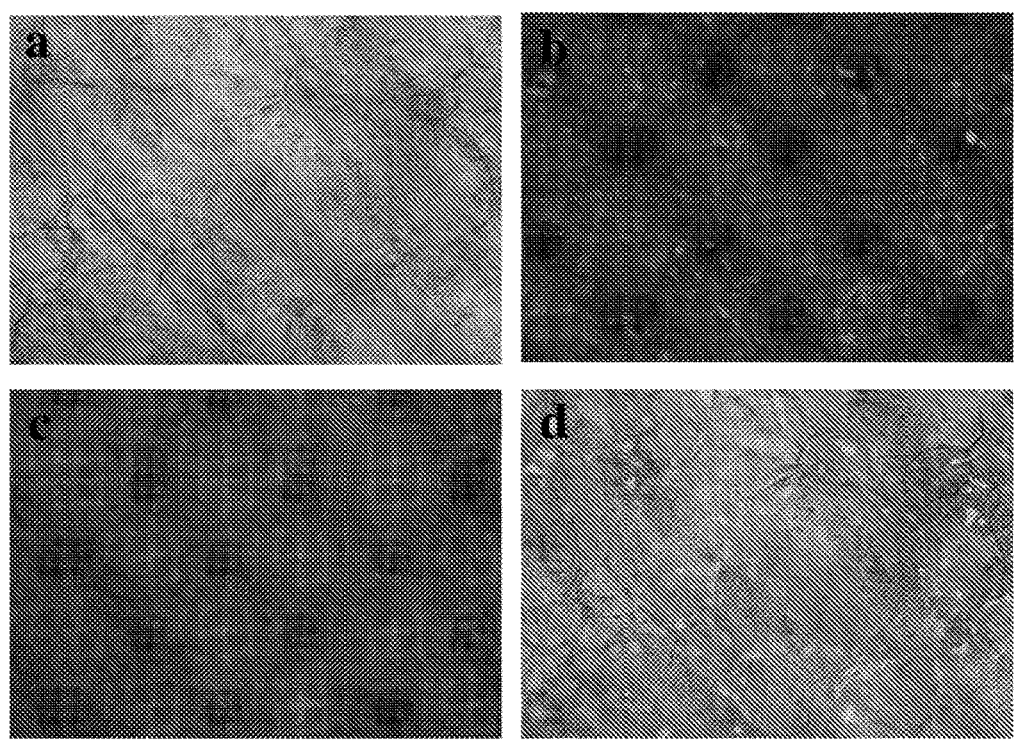
FIG. 3 shows the human mesenchymal stem cells cultured on developed matrix at Day 15 (a) Bright field view (b) Calcein-AM stained (c) DAPI stained (d) Merge.
Figure 4:
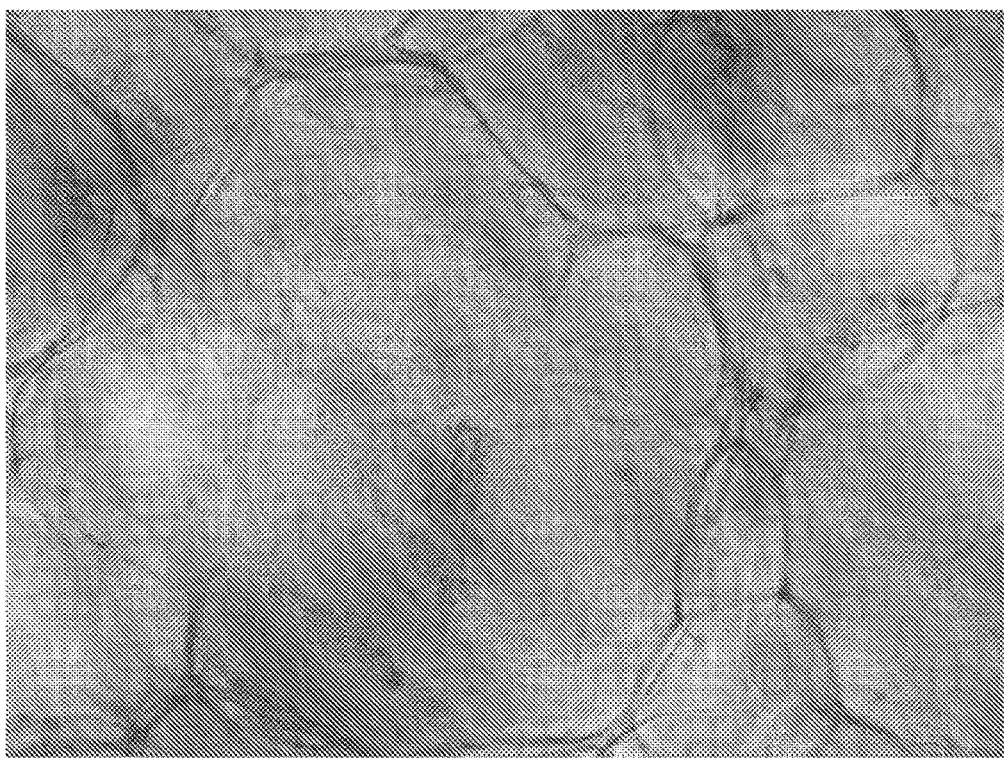
FIG. 4 shows the human mesenchymal stem cells cultured on developed matrix at Day 17.
Figure 5:
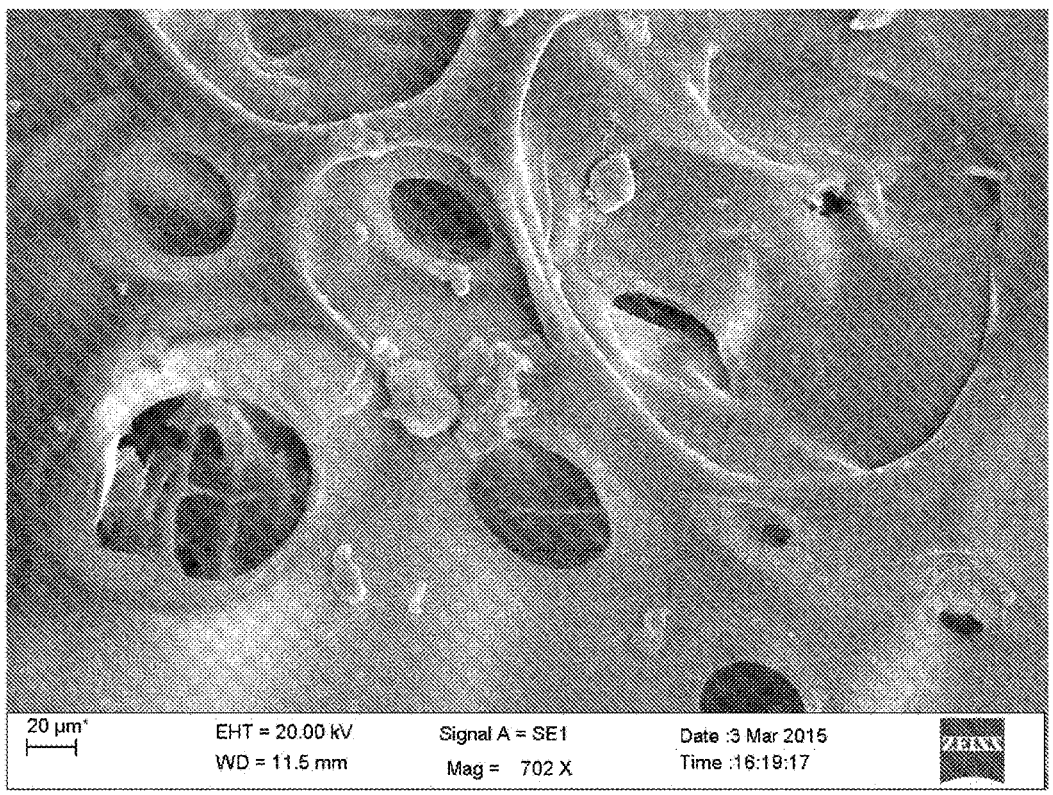
FIG. 5 shows the scanning electron microscope images developed matrix.
Figure 6:
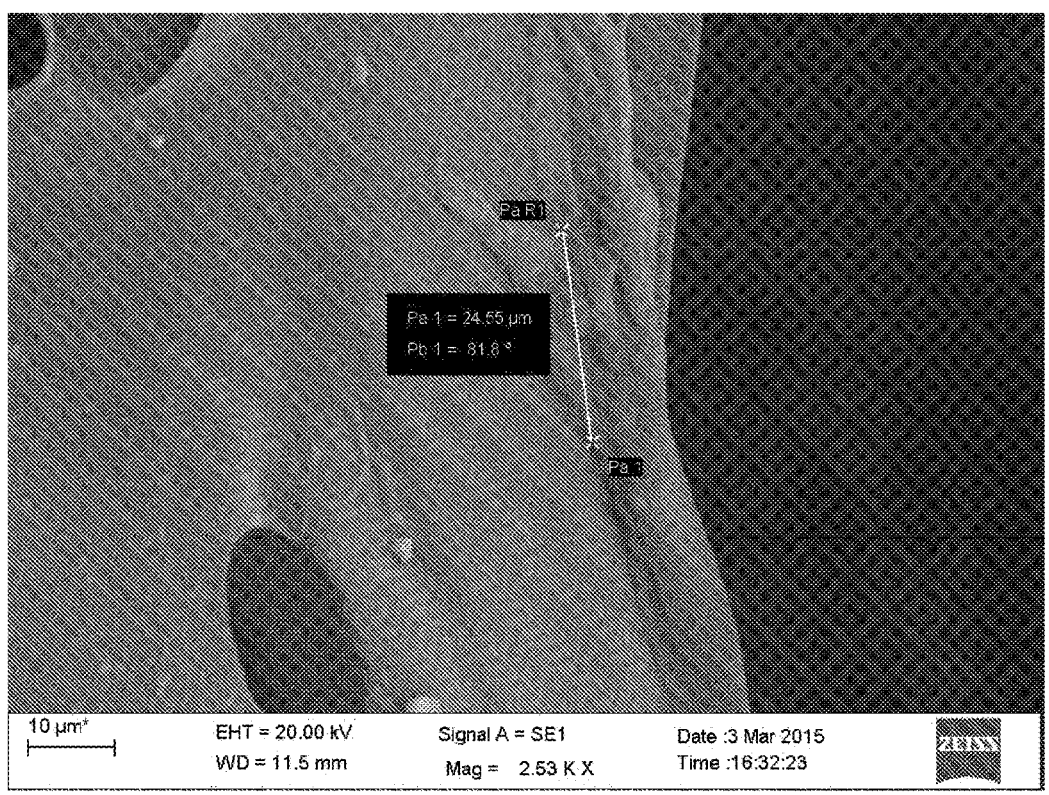
FIG. 6 shows the scanning electron microscope images of human mesenchymal stem cells cultured on developed matrix at day 15.

Accordingly, the present invention provides an improved three-dimensional scaffold polyelectrolyte complex (PEC) with high porosity, said scaffold comprising of plurality of composite polymers without using any cross-linker or leaching/foaming agents/surfactants or any integrated harmful chemicals, wherein said scaffold is non-adherent and has differential porosity and a method of preparing such scaffold.

It should be noted that the particular description and embodiments set forth in the specification below are merely exemplary of the wide variety and arrangement of instructions which can be employed with the present invention. The present invention may be embodied in other specific forms without departing from the spirit or essential characteristics thereof. All the features disclosed in this specification may be replaced by similar other or alternative features performing similar or same or equivalent purposes. Thus, unless expressly stated otherwise, they all are within the scope of present invention. Various modifications or substitutions are also possible without departing from the scope or spirit of the present invention. Therefore, it is to be understood that this specification has been described by way of the most preferred embodiments and for the purposes of illustration and not limitation.

The present invention provides a novel and unique novel and unique technique of culturing human epidermal cells into a proliferating, sub-confluent layer on a biocompatible membrane to form sheets suitable for grafting. The invention provides a ready to use biodegradable and biocompatible tissue construct with autologous/allogeneic human stem cells based product. The present invention also provides a reconstructive procedure to meet the specific requirements necessary to achieve satisfactory wound closure and also to restore functional integrity in the least time and with the least complications and morbidity. The extracellular matrix as provided by the present invention has tissue like properties and is capable of being used for wound healing. The invention is directed to bioengineered tissue constructs of cultured cells and endogenously produced extracellular matrix components without the requirement of exogenous matrix components or network support or scaffold members. The invention can thus advantageously be made entirely from human cells, and human matrix components produced by those cells, for example, when the bioengineered tissue construct is designed for use in humans. The invention is also directed to methods for producing tissue constructs by stimulation of cells in culture, such as Mesenchymal stem cells, fibroblast and keratinocytes and Mesenchymal stem cells differentiated into fibroblast and keratinocytes to produce extracellular matrix components without the addition of either exogenous matrix components, network support, or scaffold members. Further, this tissue construct can be made by seedings of Mesenchymal stem cells and fibroblast and keratinocytes and Mesenchymal stem cells differentiated fibroblast and keratinocytes cells to produce a cultured tissue construct that mimics the cell composition and tissue structures of native tissues. The tissue constructs of the invention are useful for clinical purposes such as grafting to a patient with tissue or organ defect, such as skin ulcer or wound, or for in vitro tissue testing or animal grafting such as for safety testing or validation of pharmaceutical, cosmetic, and chemical products.

The present invention uses proliferative/preconfluent Mesenchymal stem cells (MSCs), fibroblast, keratinocytes and Mesenchymal stem cells differentiated fibroblast and keratinocytes whereby cells are transferred from culture to the wound bed. This approach is advantageous over the prior art in that:

1. It aids in wound healing.
2. It ensures rapid healing of wound.
3. It ensures moist wound environment by preventing wound desiccation.
4. The grafts can be made within 15 days.
5. It is economical and offers an alternative treatment to the standard wound management therapies.
6. There is a dramatically reduced risk of transmission of infectious disease due to rigorous process controls.

The cells are grown directly on the delivery system (scaffold) such as a biocompatible polymer or biopolymer membrane. The cells with scaffold can therefore be transferred as such to the patient thus avoiding the potential damage occurring in the conventional enzymatic separation from the culture vessel. The cells are transferred while in a proliferative state. In some embodiments, the use of preconfluent cells aids in the adherence of such cells to the wound as they express an integrin profile different from fully differentiated, terminal cells. The interactive component of the invention is provided by the use of actively proliferating Mesenchymal stem cells. During tissue repair a number of cytokines, growth factors etc. are released at the wound site.

The cells at the wound site express molecules that have both an autocrine as well as a paracrine effect. The expression of these factors however depends on the stage of wound healing. Skin cells administered at the wound site would, depending on the cues present at the wound site, either upregulate/downregulate certain factors and thus help in wound repair. Thus, the cells enhance healing by interacting with the factors present at the wound site.

The uses of an artificial skin substitute are useful for both repair and regeneration. Repair indicates the process that a tissue undergoes to completely regenerate/reform. Allogeneic Mesenchymal stem cells used in this wound cover to repair the damaged skin leading to its regeneration.

In another embodiment, the process involves the optimization of scaffolds onto which cells are seeded to form a uniform tissue with scaffolds that provide physical and chemical cues to guide the process. Scaffolds may be selected from a group comprising of natural biopolymers such as chitosan and gelatin. Scaffolds take forms ranging from sponge like sheets to gels to highly complex structures with intricate pores and channels made with new materials processing technologies. The spatial and compositional properties of the scaffold, the porosity of the scaffold and interconnectivity of the pores are all required to enable cell penetration into the structure as well as the transport of nutrients and waste products.

Under the present invention the sequential timed patterned physico-chemical treatment of the two or more polymers is carried on to get air dried 3D scaffold of polyelectrolyte complex (PEC) and also at the same time using a specifically designed aspect ratio of a system for agitation/homogenization. The sequential timed patterned physico-chemical treatment of polymers can be as dissolution of gelatin at temperature 35-75° C., preferably at 60° C. using 3% of gelatin, wherein the process comprises:
 a. Stirring of the gelatin solution at 2500-3200 rpm at temp 15-30° C. for 20-30 min.
 b. Adding of acid preferably glacial acetic acid (0.5-2.5%) at rate of 1 ml/min and at temp 15-30° C. for 5-15 min.
 c. Adding of chitosan preferably 80% DAC, 1.0% final concentration at the rate of 1 mg/ml at temp 15-30° C. for 80-130 min.

Once the above method of physico-chemical treatment of polymers is complete then the process of air drying the composite solution is carried on. The air drying of the prepared composite solution is carried out at RH 5-44%, temp 5-18° C., preferable at 12° C. and 20% RH.

Further mesenchymal stem cell are seeded onto biocompatible scaffold at cell density of $0.1 \times 10^6$ to $0.5 \times 10^6$ cell/$cm^2$. The cells are monolayer and 80% to 100% confluent at the final stage of product formulation. The mesenchymal stem cells used for seeding is passage 2 to passage 5. The mesenchymal stem cell used for seeding is human mesenchymal stem cells and only pure population. The mesenchymal stem cells secrete several growth factors and cytokines (extracellular matrix) helpful in wound healing and tissue regeneration.

Further, the final product obtained will transport in semi-solid medium. The semi-solid medium is agar medium 1% to 3% and cell culture medium with essential growth factors. The agar medium contains HEPES 2-3 gm/l and sodium bicarbonate 2-3.5 gm/l. The semi-solid medium contains agar medium and cell culture medium in the ratio of 5:5, 6:4, 7:3 and 8:2 or any one of them respectively. The semi-solid medium maintains the cell viability of matrix between 60% to 90% at the temperature 4° C. to 37° C. for 28 days.

The invention is directed to bioengineered tissue constructs of cultured cells and endogenously produced extracellular matrix components without the requirement of exogenous matrix components or network support or scaffold members. The invention can thus advantageously be made entirely from human cells, and human matrix components produced by those cells, for example, when the bioengineered tissue construct is designed for use in humans.

The invention is also directed to methods for producing tissue constructs by stimulation of cells in culture, such as Mesenchymal stem cells, fibroblast and keratinocytes and Mesenchymal stem cells differentiated into fibroblast and keratinocytes to produce extracellular matrix components without the addition of either exogenous matrix components, network support, or scaffold members.

Further, this tissue construct can be made by seeding of Mesenchymal stem cells or fibroblast and keratinocytes or Mesenchymal stem cells differentiated fibroblast and keratinocytes cells to produce a cultured tissue construct that mimics the cell composition and tissue structures of native tissues.

The tissue constructs of the invention are useful for clinical purposes such as grafting to a patient with tissue or organ defect, such as skin ulcer or wound, or for in vitro tissue testing or animal grafting such as for safety testing or validation of pharmaceutical, cosmetic, and chemical products.

EXAMPLES

The following examples are for the purposes of illustration only and therefore should not be construed to limit the scope of the invention:

Example 1

Preparation of the Air-Dried Samples:
 First 100 ml of ultrapure water is taken in a beaker. Then 3 gm of gelatin is added in to the beaker containing water and dissolved by heating it. Once the solution is dissolved and heated, it is further Homogenized using stirrer. Then after this 1 ml of Acetic Acid is added and homogenized for 1 min and further 1.5 gm of chitosan is added to the solution and homogenized for 90 min. Once the mixture is homogenized, it is casted in trays and allowed to air dry. Once the sample is dried, it is cut in to the desired size.

Neutralization of the Air Dried Samples:
 The crushed samples are soaked in ammonia solution followed by washing and pat and/or vacuum dry.

Mesenchymal Stem Cells Inoculation and their Culture:
 $1 \times 10^3$ cells were seeded in the pre acclimatized scaffold (scaffold soaked in cell culture medium) and culture the cells at the day 15-18. After/between the day 15-18 scaffolds were completely filled with MSCs and rich of growth factors and nutrients.

Example 2

Cell Viability
 Cell viability of the seeded cell was evaluated through MTT colorimetric assay. Cell viability was assessed at 0 h, 24 h, 48 h and 72 h. Cells were seeded in scaffold ($1 \times 10^5$ cell/well, n=6) were incubated in 96 well plate. The MTT reagent (20 µl/well) was added to each well according to manufacturer's protocol and incubated for 3 h at 37° C. in a humidified atmosphere containing 5% $CO_2$. Cell viability was evaluated by measuring the optical density (OD) in micro-plate ELISA reader, at 570 nm and reference 630 nm. The percentage of viable cells was calculated as:

Percentage (%) viability=(Absorbance of treated cells/Absorbance of control cells)×100

Example 3

Fluorescence Microscopy
 Mesenchymal stem cells (MSCs) seeded in scaffold were evaluated through fluorescence microscope. After 15 days of cell seeding in scaffolds, cells were stained with Calcein-AM and DAPI for 30 minute. The cells were washed twice with PBS and observed under fluorescence microscope (Nikon Eclipse Ti U, Japan).

Example 4

Scanning Electron Microscopic Evaluation

Mesenchymal stem cells (MSCs) seeded in scaffold were also evaluated through scanning electron microscope. Cells with scaffolds were fixed with 3% glutaraldehyde buffer at 4° C. for 2 hrs. and analyze the scaffold in scanning electron microscope.

Example 5

Cellular viability of the Mesenchymal stem cells seeded in scaffold was evaluated at different temperature with and without $CO_2$ for transport of developed product. We have evaluated the cell viability at 4° C., 25° C. and 37° C.

We have prepared semisolid agar medium by adding some salts and culture medium and place the scaffold with cells on these semisolid medium and evaluated the cell viability at different time intervals (day 1, 3, 7, 11, 14, 18, 21, 25 and 28) by using MTT assay. The MTT reagent (20 µl/well) was added to each well according to manufacturer's protocol and incubated for 3 h at 37° C. in a humidified atmosphere containing 5% $CO_2$. Cell viability was evaluated by measuring the optical density (OD) in micro-plate ELISA reader, at 570 nm and reference 630 nm. The percentage of viable cells was calculated as:

Percentage (%) viability=(Absorbance of treated cells/Absorbance of control cells)×100

Example 6

In Vivo Efficacy Testing for the Product

Cells seeded in scaffolds were grown for 15 days and after these scaffolds with cells were applied on the surface of burn wound created on Sprague Dawley Rat (2 cm×2 cm wound created by using heated metal). Animals were sacrifice at regular time intervals (1, 4, 8, 11, 15, 18 and 22) and Histology, tissue biochemistry, blood cytokines were performed.

The prepared artificial skin substitute is potential substitute of natural skin and it helps wound healing (burn wound, diabetic foot ulcer and all type other skin wounds). Various experiments were conducted to check the said efficacy of artificial skin substitute. Cell viability, fluorescence microscopy and scanning electron microscopy confirm the cell growth and distribution at day 15. In vivo studies confirmed the potential healing property of prepared artificial skin substitute.

The obtained results of the potential and properties of the product of this invention were found considerably efficacious. It clearly indicates the technical advancement as compared to prior art.

So accordingly, the present invention provides an improved three-dimensional scaffold polyelectrolyte complex (PEC) with high porosity, said scaffold comprising of plurality of composite polymers without using any cross-linker or leaching/foaming agents/surfactants or any integrated harmful chemicals, wherein said scaffold is non-adherent and has differential porosity and a method of preparing such scaffold.

In an embodiment, said polymers are preferably selected from but not limited to gelatin, chitosan, collagen, alginate, polyvinyl alcohol, carboxy-methyl cellulose, gelatin hydrolysate, chitosan hydrolysate, partially denatured collagen and hyaluronic acid.

In another embodiment, said polymers are preferably gelatin in the range of 1%-4% and chitosan in the range of 0.5%-2.5%.

The said gelatin can be 50-300 bloom strength and DAC of chitosan can be ranging from 75%-95%.

In another embodiment, said method of preparing the scaffold comprises physico-chemical treatment; breakdown of stabilized dried air bubbles and stabilizing the scaffold.

In yet another embodiment, said method comprises sequential timed patterned physico-chemical treatment of the two or more polymers to get air dried 3D scaffold of polyelectrolyte complex (PEC) and also at the same time using a specifically designed aspect ratio of a system for agitation/homogenization.

In another embodiment, there is provided a method of preparing three-dimensional scaffold polyelectrolyte complex (PEC), said method comprises introducing the breakdown of stabilized dried air bubbles and the preparation of said PEC using a specifically designed aspect ratio of a system for stirring the polymer solution.

In another embodiment, said method comprises stabilizing the scaffold and washing followed by squeezing dry to make it ready to use as cell seeding, growth factor loading etc.

In yet another embodiment, the preferred aspect ratio are as impeller daiameter:height (2.34:1), container diameter: impeller diameter (1.3:1), impeller diameter:shaft diameter (4.4:1) and shaft out:shaft in (2.6:1).

In another embodiment, the obtained 3D scaffold is subjected to break the air bubbles applying pressure ranging from 5 kg-50 kg/$cm^2$, more preferably 0.13 bar/$cm^2$ followed by treatment with ammonia solution (7.5-25%) for 15-45 min and washing with ultrapure water (18.5 mohm) 4-5 times and squeezed to make the stable and functional scaffold for cell seeding.

In another embodiment, the obtained scaffold is freeze-dried to make the stable scaffold for seeding of autologous or allogeneic human mesenchymal stem cells (MSCs), human fibroblast, human keratinocytes, mesenchymal stem cell differentiated fibroblast and keratinocytes.

In another embodiment, the mesenchymal stem cells are seeded onto biocompatible scaffold at cell density of 0.1× $10^6$ to 0.5×$10^6$ cell/$cm^2$.

In yet another embodiment, the cells are monolayer and 80% to 100% confluent at the final stage of product formulation.

In another embodiment, the cells seeded on scaffold are cultured in serum free and xenofree medium.

In another embodiment, the mesenchymal stem cells are Autologous or allogeneic or both.

In another embodiment, the mesenchymal stem cells secrete several growth factors and cytokines (extracellular matrix) helpful in wound healing and tissue regeneration.

In another embodiment, the final product is transported in semi-solid medium.

In another embodiment, the semi-solid medium provides nutrients and support to matrix.

In another embodiment, semi-solid medium is agar medium (1% to 3%) with cell culture medium contains essential growth factors.

In another embodiment, the agar medium contains HEPES 2-3 gm/l and sodium bicarbonate 2-4 gm/l.

In another embodiment, the semi-solid medium contains agar medium and cell culture medium in the ratio of 5:5, 6:4, 7:3 and 8:2 or any one of them respectively.

In another embodiment, the semi-solid medium maintains the cell viability of matrix between 60% to 90% at the temperature 4° C. to 37° C. for 28 days.

ADVANTAGES OF THE INVENTION

The scaffold of the present invention does not stick to the wound.

The present invention comprises of improved wound hygiene.

Can be manufactured in any size and shape as per the requirement.

Easy to handle.

Multiple products can be applied for larger wounds.

Can be removed easily.

Environment friendly as it is degradable easily.

It aids in wound healing.

It ensures rapid healing of wound.

It ensures moist wound environment by preventing wound desiccation.

The grafts can be made within 15 days.

It is economical and offers an alternative treatment to the standard wound management therapies.

There is a dramatically reduced risk of transmission of infectious disease due to rigorous process controls.

What is claimed is:

1. An artificial skin substitute for wound healing, comprising:
a biocompatible and biodegradable polymer membrane consisting essentially of gelatin and chitosan as a three-dimensional scaffold polyelectrolyte complex (PEC); and
a sub-confluent and grown monolayer of at least one of human mesenchymal stem cells, human fibroblast and human keratinocytes, and human mesenchymal stem cells differentiated into fibroblast and keratinocytes and on the biocompatible and biodegradable polymer membrane, wherein the three-dimensional scaffold PEC comprises a dried and homogenized polymer formed from a gelatin polymer solution in the range of 1% to 4% and chitosan in the range of 0.5% to 2.5%, and wherein the gelatin has a 50 to 300 bloom strength and the chitosan has a Deacetylation Degree (DAC) of 75% to 95%.

2. The artificial skin substitute according to claim 1, wherein said sub-confluent and grown monolayer of at least one of human mesenchymal stem cells, human fibroblast and human keratinocytes, and human mesenchymal stem cells differentiated into fibroblast and keratinocytes are seeded at a cell density of $0.1 \times 10^6$ to $0.5 \times 10^6$ cells/cm$^2$ on the biocompatible and biodegradable polymer membrane.

3. The artificial skin substitute according to claim 1, wherein said sub-confluent and grown monolayer of at least one of human mesenchymal stem cells, human fibroblast and human keratinocytes, and human mesenchymal stem cells differentiated into fibroblast and keratinocytes are 80% to 100% confluent.

4. The artificial skin substitute according to claim 1, further comprising a serum free and xenofree medium on which the at least one of human mesenchymal stem cells, human fibroblast and human keratinocytes, and human mesenchymal stem cells differentiated into fibroblast and keratinocytes are cultured on the biocompatible and biodegradable polymer membrane.

5. The artificial skin substitute according to claim 1, wherein said at least one of human mesenchymal stem cells, human fibroblast and human keratinocytes, and human mesenchymal stem cells differentiated into fibroblast and keratinocytes are autologous or allogeneic or both.

6. An artificial skin substitute for wound healing, comprising:
a biocompatible and biodegradable polymer membrane consisting essentially of gelatin and chitosan as a three-dimensional scaffold polyelectrolyte complex (PEC); and
a sub-confluent and grown monolayer of at least one of human mesenchymal stem cells, human fibroblast and human keratinocytes, and human mesenchymal stem cells differentiated into fibroblast and keratinocytes and on the biocompatible and biodegradable polymer membrane, wherein the three-dimensional scaffold PEC comprises a dried and homogenized polymer formed from a sequential timed and patterned physico/chemical treatment of a gelatin polymer solution in the range of 1% to 4% and chitosan in the range of 0.5% to 2.5%, and wherein the gelatin has a 50 to 300 bloom strength and the chitosan has a Deacetylation Degree (DAC) of 75% to 95%; and
a semi-solid transport medium on which the biocompatible and biodegradable polymer membrane is supported.

7. The artificial skin substitute according to claim 6, wherein the semi-solid transport medium includes nutrients.

8. The artificial skin substitute according to claim 6, wherein said semi-solid transport medium comprises a 1% to 3% agar medium.

9. The artificial skin substitute according to claim 6, wherein said semi-solid transport medium comprises an agar medium comprising HEPES at a concentration of 2-3 gm/l and sodium bicarbonate at a concentration of 2-4 gm/l.

10. The artificial skin substitute according to claim 6, wherein said semi-solid transport medium comprises an agar medium and cell culture medium in the ratio of 5:5, 6:4, 7:3, and 8:2.

11. The artificial skin substitute according to claim 6, wherein said semi-solid transport medium comprises an agar medium that maintains cell viability on the biocompatible and biodegradable polymer membrane between 60% to 90% at a temperature of 4° C. to 37° C. for 28 days.

12. The artificial skin substitute according to claim 6, wherein said sub-confluent and grown monolayer of at least one of human mesenchymal stem cells, human fibroblast and human keratinocytes, and human mesenchymal stem cells differentiated into fibroblast and keratinocytes are seeded at a cell density of $0.1 \times 10^6$ to $0.5 \times 10^6$ cells/cm$^2$ on the biocompatible and biodegradable polymer membrane.

13. The artificial skin substitute according to claim 6, wherein said sub-confluent and grown monolayer of at least one of human mesenchymal stem cells, human fibroblast and human keratinocytes, and human mesenchymal stem cells differentiated into fibroblast and keratinocytes are 80% to 100% confluent.

14. The artificial skin substitute according to claim 6, further comprising a serum free and xenofree medium on which the at least one of human mesenchymal stem cells, human fibroblast and human keratinocytes, and human mesenchymal stem cells differentiated into fibroblast and keratinocytes are cultured on the biocompatible and biodegradable polymer membrane.

15. The artificial skin substitute according to claim 6, wherein said at least one of human mesenchymal stem cells, human fibroblast and human keratinocytes, and human mesenchymal stem cells differentiated into fibroblast and keratinocytes are autologous or allogeneic or both.

* * * * *